US011497595B2

(12) United States Patent
Tarabein et al.

(10) Patent No.: US 11,497,595 B2
(45) Date of Patent: Nov. 15, 2022

(54) BIODEGRADABLE STENT

(71) Applicant: BOSTON SCIENTIFIC SCIMED, INC., Maple Grove, MN (US)

(72) Inventors: Karim Tarabein, Shaker Heights, OH (US); James J. Scutti, Arlington, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 16/672,138

(22) Filed: Nov. 1, 2019

(65) Prior Publication Data

US 2020/0138559 A1    May 7, 2020

Related U.S. Application Data

(60) Provisional application No. 62/754,993, filed on Nov. 2, 2018.

(51) Int. Cl.
*A61F 2/04* (2013.01)
*A61F 2/06* (2013.01)

(52) U.S. Cl.
CPC .......... *A61F 2/04* (2013.01); *A61F 2/06* (2013.01); *A61F 2002/041* (2013.01); *A61F 2002/044* (2013.01); *A61F 2002/045* (2013.01); *A61F 2210/0004* (2013.01); *A61F 2250/003* (2013.01); *A61F 2250/0004* (2013.01)

(58) Field of Classification Search
CPC ...... A61F 2/04; A61F 2/82; A61F 2/86; A61F 2/90; A61F 2/06; A61F 2002/041; A61F 2002/045; A61F 2002/044; A61F 2002/046; A61F 2002/0004; A61F 2002/003; A61F 2250/0071; A61F 2250/0082

See application file for complete search history.

(56) References Cited

U.S. PATENT DOCUMENTS

| 5,957,975 | A | 9/1999 | Lafont et al. |
|---|---|---|---|
| 7,641,983 | B2 | 1/2010 | Stinson |
| 7,651,527 | B2 | 1/2010 | Krivoruchko et al. |
| 7,833,261 | B2 * | 11/2010 | Chen .................. A61F 2/89 623/1.16 |
| 7,955,381 | B1 | 6/2011 | Wang et al. |
| 8,057,534 | B2 | 11/2011 | Boismier et al. |

(Continued)

OTHER PUBLICATIONS

International Search Report and Written Opinion dated Apr. 21, 2020 for International Application No. PCT/US2019/059521.

*Primary Examiner* — Brian A Dukert
(74) *Attorney, Agent, or Firm* — Seager, Tufte & Wickhem, LLP

(57) ABSTRACT

Medical stent designs are disclosed. An example stent includes a tubular scaffold having a proximal end and a distal end. The tubular scaffold includes a first filament extending between the proximal end and the distal end, the first filament including a first biodegradable region positioned adjacent to a second biodegradable region. Further, the first biodegradable region includes a first biodegradable material, the first biodegradable material having a first rate of degradation. The second biodegradable region includes a second biodegradable material, the second biodegradable material having a second rate of degradation, wherein the first rate of degradation is different from the second rate of degradation.

18 Claims, 15 Drawing Sheets

(56) References Cited

U.S. PATENT DOCUMENTS

| | | |
|---|---|---|
| 8,062,351 B2 | 11/2011 | Burnside et al. |
| 8,267,990 B2 | 9/2012 | Gale et al. |
| 8,388,676 B2 | 3/2013 | Stinson |
| 8,394,488 B2 | 3/2013 | Dave et al. |
| 8,709,070 B2 | 4/2014 | Wang et al. |
| 8,764,813 B2 * | 7/2014 | Jantzen ................ A61F 2/915 623/1.13 |
| 8,870,945 B2 | 10/2014 | Dave et al. |
| 8,961,585 B2 | 2/2015 | Ma et al. |
| 9,248,034 B2 | 2/2016 | Hossainy et al. |
| 9,283,097 B2 | 3/2016 | Wang et al. |
| 9,326,870 B2 | 5/2016 | Berglund et al. |
| 9,333,099 B2 * | 5/2016 | Pacetti ................ A61F 2/915 |
| 9,474,637 B2 | 10/2016 | Zhao |
| 9,561,308 B2 | 2/2017 | Schaffer |
| 10,028,851 B2 | 7/2018 | Dugan et al. |
| 10,105,246 B2 | 10/2018 | Liu |
| 2005/0043783 A1 * | 2/2005 | Amis ................ A61F 2/88 623/1.22 |
| 2007/0254012 A1 | 11/2007 | Ludwig et al. |
| 2008/0199510 A1 * | 8/2008 | Ruane ................ B82Y 30/00 424/426 |
| 2010/0004733 A1 | 1/2010 | Atanasoska et al. |
| 2010/0087916 A1 | 4/2010 | Bayer et al. |
| 2010/0292776 A1 | 11/2010 | Weber et al. |
| 2011/0022158 A1 | 1/2011 | Atanasoska et al. |
| 2011/0046721 A1 | 2/2011 | Arps |
| 2011/0319977 A1 | 12/2011 | Pandelidis et al. |
| 2013/0138219 A1 | 5/2013 | Toomey et al. |
| 2013/0144376 A1 | 6/2013 | Dave et al. |
| 2013/0184809 A1 | 7/2013 | Stinson |
| 2015/0057745 A1 | 2/2015 | Gale et al. |
| 2015/0342764 A1 | 12/2015 | Ramzipoor et al. |
| 2017/0119936 A1 * | 5/2017 | Schaffer ................ A61F 2/86 |
| 2019/0209354 A1 * | 7/2019 | Scanlon ................ B29C 53/04 |

\* cited by examiner

BIODEGRADABLE STENT

CROSS-REFERENCE TO RELATED APPLICATIONS

This application claims priority under 35 U.S.C. § 119 to U.S. Provisional Application Ser. No. 62/754,993, filed Nov. 2, 2018, the entirety of which is incorporated herein by reference.

TECHNICAL FIELD

The present disclosure pertains to medical devices, and methods for manufacturing medical devices. More particularly, the present disclosure pertains to elongated intracorporeal medical devices including medical stents and methods for manufacturing and using such devices.

BACKGROUND

Stents are utilized in a variety of medical procedures and situations, and accordingly, their structure and function are well known. A stent is generally a tubular prosthesis that is introduced via a catheter into a body lumen. The stent is introduced into the body lumen with a generally reduced diameter and subsequently expanded to the diameter of the body lumen. In its expanded configuration, the stent may support and reinforce the wall of the body lumen while maintaining the body lumen in an open, unobstructed condition.

In some instances, utilizing a medical stent to treat a target site may only require temporary placement of the stent. For example, in some instances it may be beneficial to implant a stent at a target site for a limited period of time, after which it may be desirable to remove the stent (for example, after completion of the treatment). However, it can be appreciated that trauma, such as tearing or similar damage to the wall of the body lumen may occur if the stent is forcibly removed from the body lumen. Accordingly, in some instances it may be desirable to design the stent to biodegrade in a controlled manner after the prescribed treatment period. Examples described herein disclose a stent designed to biodegrade in a controlled manner after a prescribed treatment period.

BRIEF SUMMARY

This disclosure provides design, material, manufacturing method, and use alternatives for medical devices, such as medical stents. An example stent includes a tubular scaffold having a proximal end and a distal end. The tubular scaffold includes a first filament extending between the proximal end and the distal end and the first filament includes a first biodegradable region positioned adjacent to a second biodegradable region. Further, a portion of the first filament within the first biodegradable region has a first rate of degradation, a portion of the first filament within the second biodegradable region has a second rate of degradation and the first rate of degradation is different from the second rate of degradation.

Alternatively or additionally to any of the embodiments above, wherein the first biodegradable region includes a catalyst disposed on the first filament.

Alternatively or additionally to any of the embodiments above, wherein the first catalyst includes an enzyme.

Alternatively or additionally to any of the embodiments above, wherein the first catalyst includes a ferric particle.

Alternatively or additionally to any of the embodiments above, wherein the first catalyst is configured to be activated by an activation source, wherein the activation source triggers the first catalyst to accelerate the rate of degradation of the first biodegradable material.

Alternatively or additionally to any of the embodiments above, wherein the activation source includes an activation fluid.

Alternatively or additionally to any of the embodiments above, wherein the activation source includes inductive heating.

Alternatively or additionally to any of the embodiments above, wherein the first catalyst is disposed along an outer surface of the first filament.

Alternatively or additionally to any of the embodiments above, wherein the tubular scaffold further comprises a second filament positioned adjacent to the first filament at a first activation site, and wherein the first catalyst extends between the first filament and the second filament.

Alternatively or additionally to any of the embodiments above, further comprising a second catalyst positioned along the first filament at a third biodegradable region, wherein the second catalyst is configured to accelerate degradation of the third biodegradable region at a third degradation rate different from the first rate of degradation, the second rate of degradation or both the first and the second rates of degradation.

Alternatively or additionally to any of the embodiments above, wherein the first biodegradable material encases the second biodegradable material.

Alternatively or additionally to any of the embodiments above, wherein the second rate of degradation is slower than the first rate of degradation.

Alternatively or additionally to any of the embodiments above, wherein the first biodegradable material, the second biodegradable material, or both the first and the second biodegradable materials are multiphasic.

Alternatively or additionally to any of the embodiments above, wherein the second biodegradable region is devoid of the second biodegradable material.

Alternatively or additionally to any of the embodiments above, wherein the second biodegradable region includes a catalyst disposed on the first filament.

Another example stent includes a tubular scaffold having a proximal end and a distal end. The tubular scaffold includes a first filament extending between the proximal end and the distal end and a second filament extending between the proximal end and the distal end. The first filament crosses the second filament at a first activation site. An activation material including a first catalyst is disposed along the first activation site. The activation material extends between the first and second filaments. The first catalyst is configured to dissolve portions of the first and second filaments in contact with the first catalyst at a faster rate than portions of the first and second filaments which are devoid of the catalyst.

Alternatively or additionally to any of the embodiments above, wherein the catalyst includes an enzyme.

Alternatively or additionally to any of the embodiments above, further comprising a second activation site located along the first filament, and wherein a second catalyst is disposed along the second activation site, and wherein the degradation rate of the second catalyst is different from the degradation rate of the first catalyst.

Another example stent includes a tubular scaffold having a proximal end and a distal end. The tubular scaffold includes a plurality of filaments extending between the proximal end and the distal end. Each filament includes a first biodegradable material having a first rate of degradation and a second biodegradable material having a second rate of degradation. Further, the first rate of degradation is faster than the second rate of degradation, the second biodegradable material is surrounded by the first biodegradable material and the second material is located in a plurality of discontinuous regions within the first biodegradable material.

Alternatively or additionally to any of the embodiments above, further comprising a catalyst disposed along discrete portions of each of the plurality of filaments, wherein the catalyst includes an enzyme.

Alternatively or additionally, the discrete portions have cross-sections only including the first biodegradable material.

Alternatively or additionally, the discrete portions have cross-sections devoid of the second biodegradable material.

Alternatively or additionally, the catalyst directly contacts the first biodegradable material.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
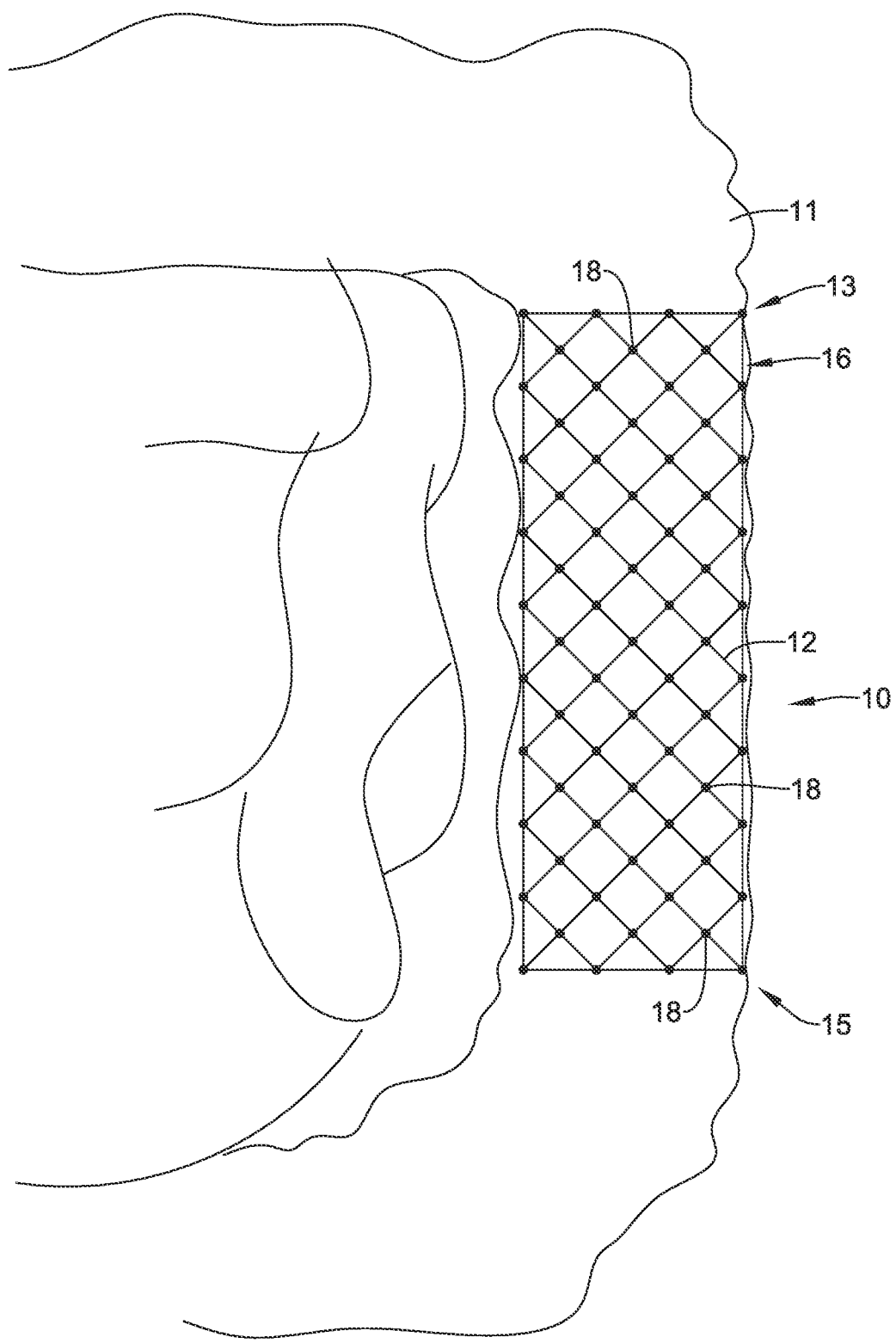
FIG. 1 illustrates an example stent positioned within a body cavity.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

FIG. 1 shows an example stent 10 positioned in a body lumen 11 (e.g., large intestine). While FIG. 1 illustrates the example stent 10 positioned in the large intestine 11, it is contemplated that the stent 10 (and other example stents disclosed herein) may be utilized in a variety of body lumens and/or cavities. For example, stent 10 may be utilized to treat the bile duct, pancreatic duct, esophagus, large intestine, small intestine, peripheral arteries, coronary arteries, veins, neurovasculature or other similar body lumens and/or cavities.

As illustrated in FIG. 1, stent 10 may include a tubular scaffold 16. The tubular scaffold 16 may include a first, proximal end 13 and a second, distal end 15. Additionally, the tubular scaffold 16 may include a plurality of filaments and/or strut members 12 extending from the proximal end 13 to the distal end 15. The filaments 12 may be arranged and/or engaged with one another in a variety of different arrangements and/or geometric patterns. In some examples, the filaments 12 may be laser cut from a unitary tubular member. In other examples, the filaments 12 may be one or more, or a plurality of wires braided, woven, knitted or constructed using a combination of these (or similar) manufacturing techniques. Therefore, numerous designs, patterns and/or configurations for the stent cell openings, strut thicknesses, strut designs, stent cell shapes are contemplated and may be utilized with embodiments disclosed herein.

The stent 10 may be delivered to a treatment area via a stent delivery system (not shown). For example, in some instances the stent 10 may be a balloon expandable stent. In some instances, balloon expandable stents may be manufactured from a single, cylindrical tubular member (e.g., a cylindrical tubular member may be laser cut to form a balloon expandable stent).

In other examples, the stent 10 may be a self-expanding stent. A self-expanding stent may be delivered to a treatment area in a radially constrained configuration via a self-expanding stent delivery system, and then released from the stent delivery system to automatically radially expand to a deployed configuration when unconstrained by the stent delivery system. It is contemplated that the examples disclosed herein may be utilized with any one of various stent configurations, including, balloon expandable stents, such as a laser cut stent and/or a braided stent, a self-expanding stent, non-expandable stents, or other stents.

The stent filaments 12 disclosed herein may be constructed from a variety of materials. For example, the filaments 12 may be constructed from a metal (e.g., Nitinol). In other instances, the filaments 12 may be constructed from a polymeric material (e.g., PET). In yet other instances, the filaments 12 may be constructed from a combination of metallic and polymeric materials. Further, the filaments 12 may include a bioabsorbable and/or biodegradable material. While not illustrated in FIG. 1, the stent 10 may include a flared region (e.g., a flared portion adjacent the proximal end 13 and/or the distal end 15).

FIG. 1 further illustrates that the stent 10 may include one or more "activation sites" 18 disposed at discrete locations along the tubular scaffold 16. As will be described in greater detail below, each individual activation site 18 may define a region along the tubular scaffold 16 whereby an "activation material" including a catalyst (e.g., accelerator, etc.) may be disposed while remaining portions of the tubular scaffold 16 may be devoid of the activation material. Further, the catalyst may be designed to accelerate the biodegradation and/or bioabsorption of the underlying tubular scaffold material at the activation sites 18. While FIG. 1 illustrates that the activation sites 18 may be located at the intersection (e.g., crossing) of two stent filaments 12, it is contemplated that the activation sites 18 may be located at any region along the tubular scaffold 16, leaving other regions of the tubular scaffold 16 devoid of activation sites 18.

Figure 2:
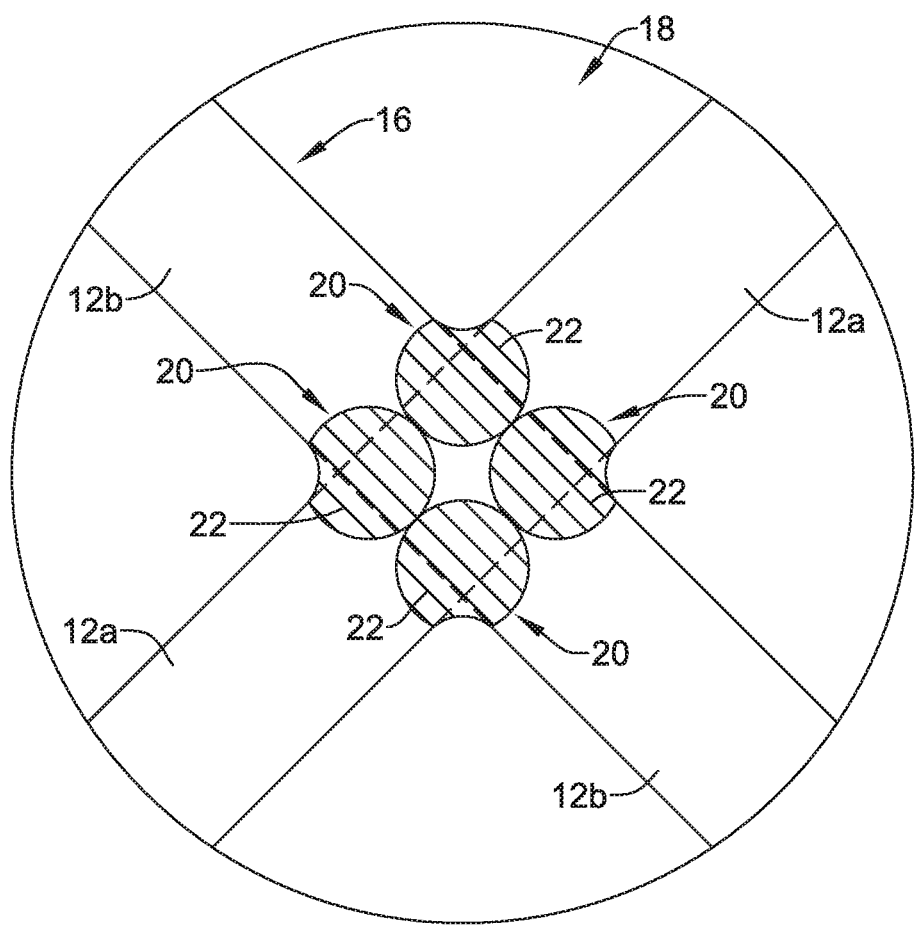
FIG. 2 is a detailed view of a portion of the example stent shown in FIG. 1.

FIG. 2 is a detailed view of an example activation site 18 located on the tubular scaffold 16 described above. As illustrated in FIG. 2, the activation site 18 may be located at the intersection of a first filament 12a and a second filament 12b of the tubular scaffold 16. The activation site 18 may include an activation material 20 disposed along the outer surface of the first filament 12a, the second filament 12b or both the first filament 12a and the second filament 12b. Portions of the first filament 12a and the second filament 12b extending beyond the activation site 18 may be devoid of the activation material 20. In some examples, the activation material 20 may extend from the first filament 12a to the second filament 12b, thereby coupling the first filament 12a to the second filament 12b. While the activation material 20 may couple the first filament 12a to the second filament 12b, it can be appreciated that the activation material 20 may be designed to permit the first filament 12a to flex, slide, pivot, and/or shift with respect to the second filament 12b.

As discussed above, in some instances the activation material 20 may include a catalyst material 22. Further, the catalyst 22 may be mixed with (e.g., suspended within) another biodegradable or non-biodegradable base material (not shown in FIG. 2) to define the activation material. However, in other examples the activation material 20 may be constructed entirely from the catalyst material 22. Additionally, the catalyst 22 may be designed to accelerate the biodegradation of the tubular scaffold 16 material with which it is in contact with. For example, the catalyst 22 may be designed to accelerate the biodegradation of the portions of the first filament 12a and/or the second filament 12b with which the catalyst 22 directly contacts.

In some examples, the catalyst 22 may include an enzyme. For example, the catalyst 22 may include (but is not limited to) proteases, esterases, glycosidases, manganese peroxidases, and/or similar materials. Further, it is contemplated that for examples in which the tubular scaffold 16 is constructed of a biodegradable polymer, the catalyst 22 may be designed to include an enzyme which is designed to break down (e.g., biodegrade) the particular biodegradable polymer utilized to construct the tubular scaffold 16 (e.g., the material utilized to construct the first filament 12a and/or the second filament 12b in FIG. 2). The enzymes contemplated herein may include, but are not limited to, plant enzymes, microbial enzymes, mammalian enzymes and/or human enzymes.

In some examples, the catalyst 22 utilized in the activation material 20 may be "activated" (e.g., triggered) to begin degradation of the material on which it is disposed via an "activation source" (not shown in FIG. 2). The activation source may include a variety of materials, methods, processes, etc. In some examples, enzymatic catalysts may be activated via contact with one or more fluids which may be present naturally in the body (and, therefore, may come in contact with the catalyst material). In other examples, the catalyst may include a fluid which is injected into the body by a clinician, whereby the fluid is designed to contact and activate the catalyst. As discussed above, activation of the catalyst may cause material in direct contact with the catalyst (e.g., material used to construct the tubular scaffold 16) to degrade at an accelerated rate relative to the tubular scaffold material which is not in direct contact with the catalyst.

In yet other examples, the catalyst 22 may include one or more ferric particles. In some examples, the ferric particle catalysts may be activated via inductive heating using an MRI. Additionally, it is contemplated that other heat sources may be utilized to activate the ferric particle catalyst. As discussed above, activation of the ferric catalyst may cause material in direct contact with the catalyst (e.g., material used to construct the tubular scaffold 16) to degrade at an accelerated rate relative to tubular scaffold material which is not in direct contact with the catalyst.

Figure 3:
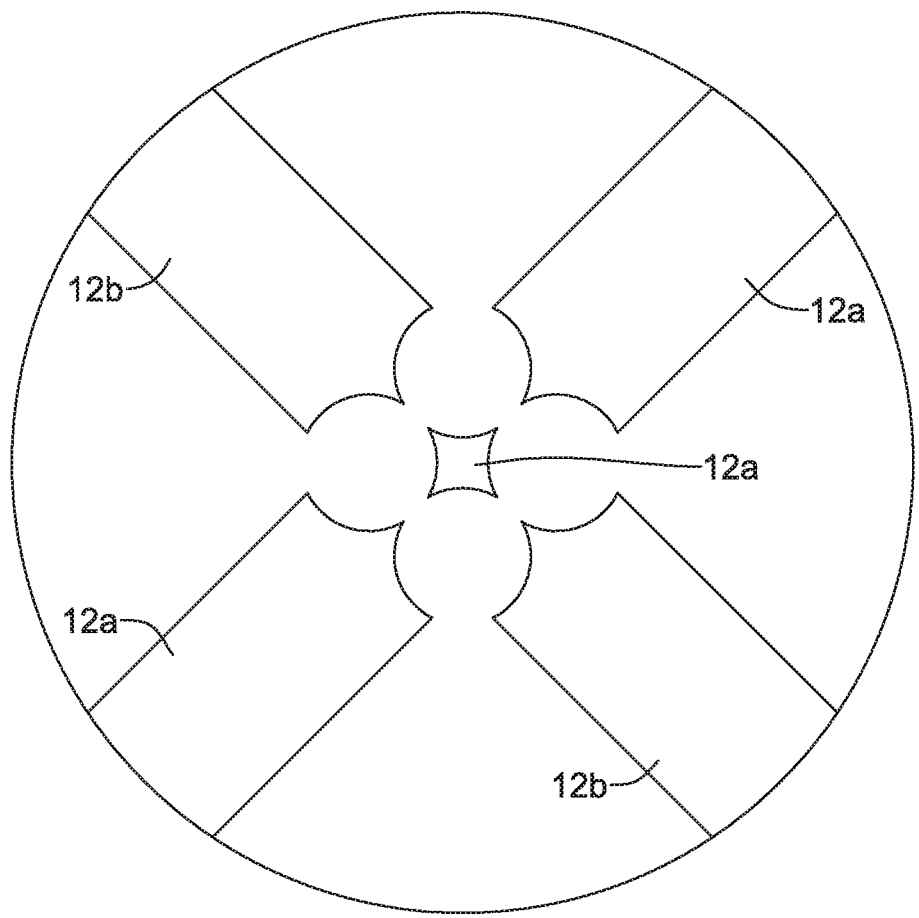
FIG. 3 illustrates a portion of the example stent shown in FIG. 1 in a fragmented state.

FIG. 3 illustrates the activation site 18 shown in FIG. 2 after a portion of each of the first filament 12a and the second filament 12b have biodegraded (e.g., dissolved). It can be appreciated from the above discussion that the portions of the first filament 12a and the second filament 12b which have dissolved include those portions of the first filament 12a and the second filament 12b which were in contact with the activation material 20 and catalyst 22 (discussed with respect to FIG. 2).

As stated above, in some instances the material used to construct the tubular scaffold 16 (including the first filament 12a and the second filament 12b) may include a biodegradable material. Accordingly, the biodegradable material of the tubular scaffold 16 may biodegrade at a rate inherent to its material composition. However, as discussed above, the catalyst 22 present in the activation material 20 may accelerate the biodegradation rate of the base biodegradable material of the tubular scaffold 16 at discrete locations, i.e., at the activation sites 18 along the stent 10. In such instances, the material in contact with the activation material 20 (and, hence, the catalyst 22) may dissolve faster than material adjacent to the activation material 20 (e.g., portions of the tubular scaffold which are not in contact with the catalyst). Accordingly, as different portions of the tubular scaffold 16 biodegrade at different rates, the tubular scaffold 16 may fragment into portions of varying size. Some of these fragments may dissolve at the rate inherent to the material of the tubular scaffold 16, and therefore, may remain in the body longer than faster dissolving material (e.g., material in contact with the catalyst). For example, FIG. 3 illustrates the fragments of the tubular scaffold 16 which remain after the portions of the first filament 12a and the second filament 12b in contact with the catalyst 22 have dissolved. As discussed above, these portions may eventually dissolve, just not as quickly as the portions of the first filament 12a and the second filament 12b which had been in contact with the catalyst 22.

Figure 4:
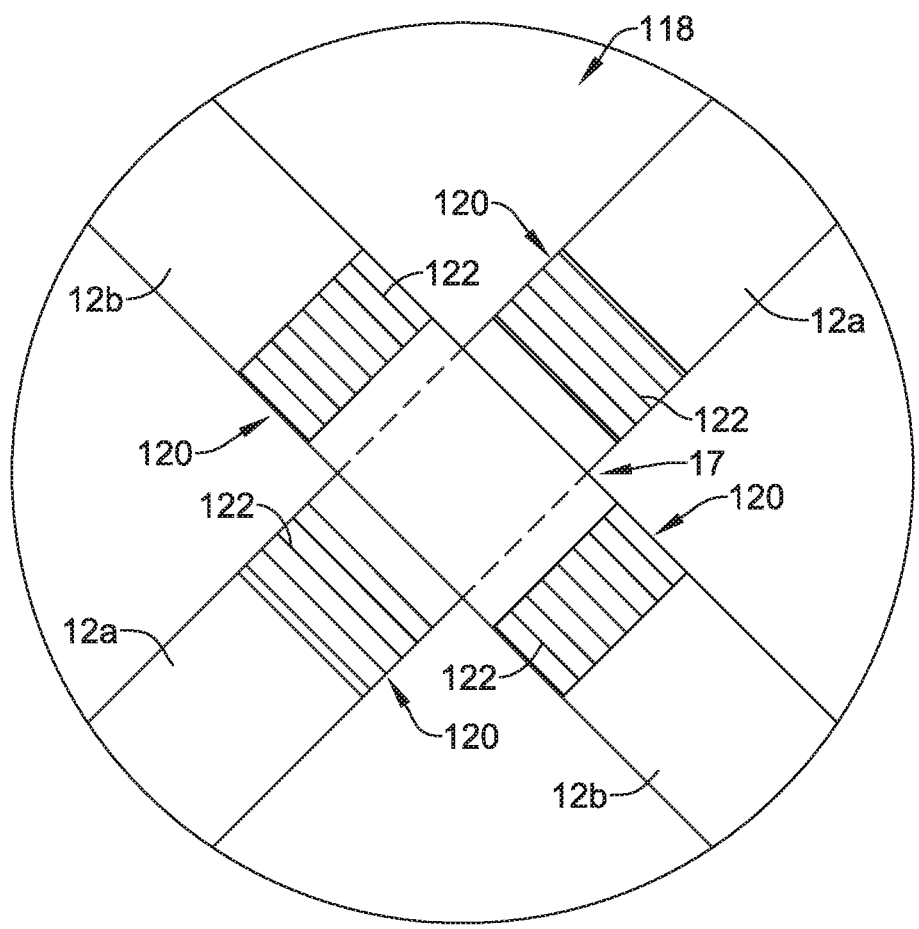
FIG. 4 illustrates a portion of another example stent.

FIG. 4 illustrates another example activation site 118. The activation site 118 may be similar in form and function to the activation site 18 described above. In other words, the activation site 118 may be another example activation site disposed along the tubular scaffold 16 described above. Accordingly, the activation site 118 illustrates the first filament 12a intersecting with the second filament 12b. However, FIG. 4 further illustrates activation material 120 (including a catalyst 122) disposed along discrete portions of the first filament 12a and the second filament 12b while portions of the first filament 12a and the second filament 12b extending beyond the activation site 118 may be devoid of the activation material 120. In the example shown in FIG. 4, the activation material 120 may not extend between the first filament 12a and the second filament 12b, as described above with respect to FIG. 2. Rather, the activation material 120 may be positioned away from the intersection 17, such as a crossover point or convergence of the first filament 12a and the second filament 12b.

Figure 5:
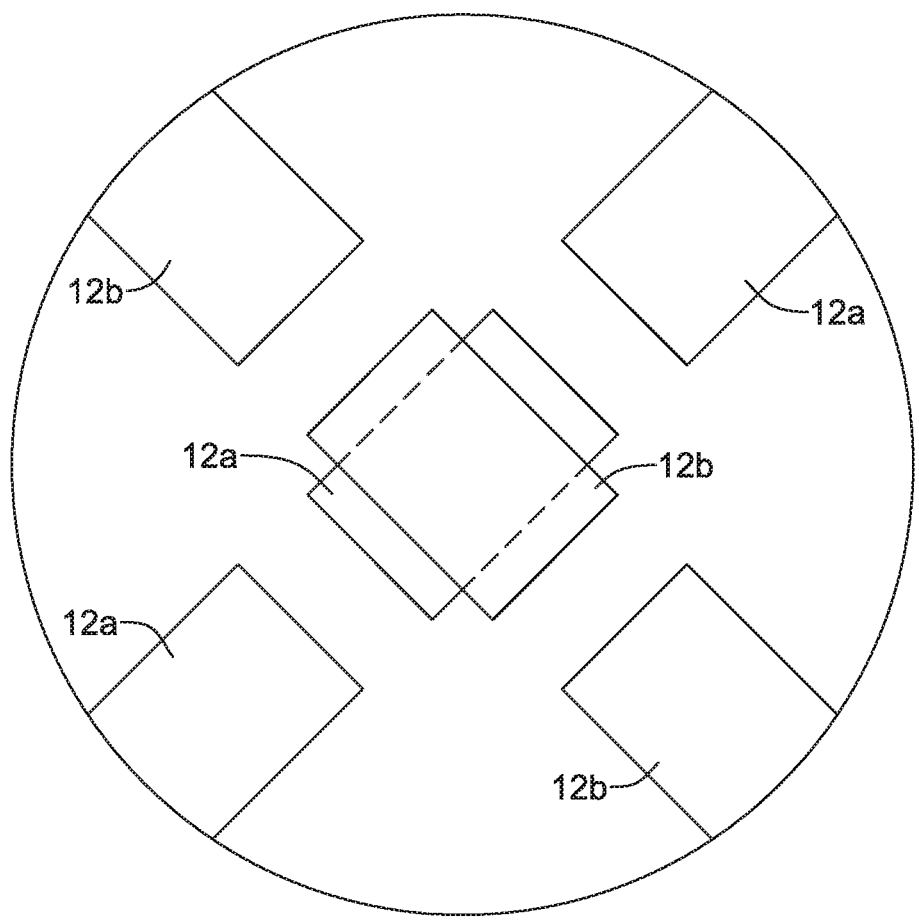
FIG. 5 illustrates a portion of the example stent shown in FIG. 4 in a fragmented state.

Similar to that described above with respect to FIG. 3, FIG. 5 illustrates the fragments of the first filament 12a and the second filament 12b (shown in FIG. 4) remaining after the portions of the first filament 12a and the second filament 12b in contact with the catalyst 122 have dissolved.

Figure 6:
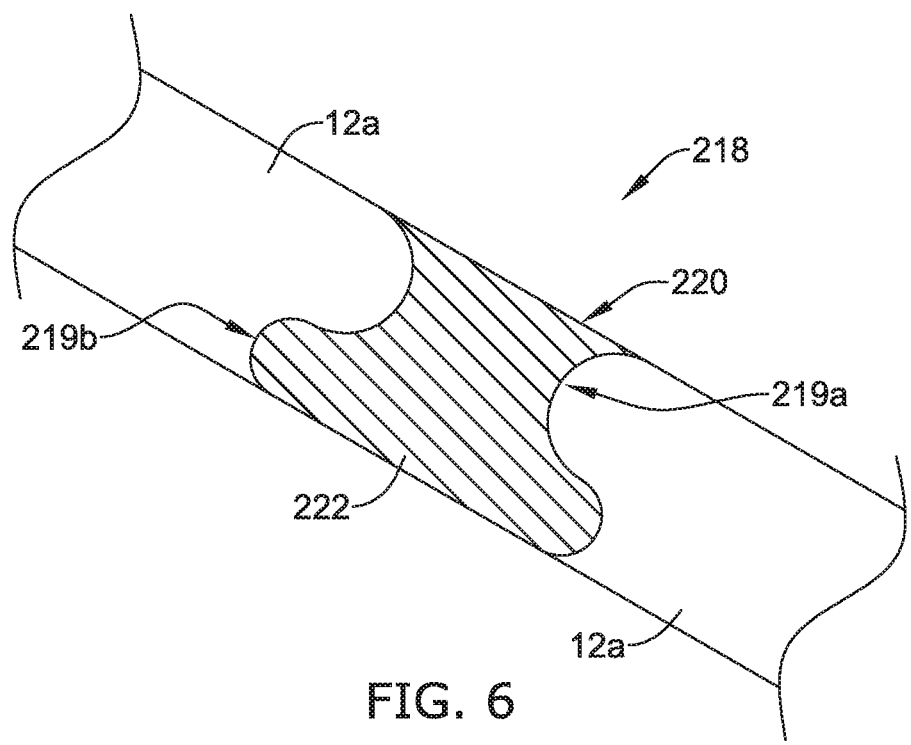
FIG. 6 illustrates a portion of another example stent.

FIG. 6 illustrates another example activation site 218. The activation site 218 may be similar in form and function to other activation sites described herein. For example, FIG. 6 illustrates an activation material 220 (including a catalyst 222) disposed along discrete portions of the first filament 12a while other portions of the first filament 12a extending beyond the activation site 218 may be devoid of the activation material 220. FIG. 6 illustrates that the activation material 220 may be applied such that it includes one or more curved portions 219a. It can be appreciated that the activation material 220 may be disposed along the first filament 12a in a variety of shapes and/or arrangements.

Figure 7:
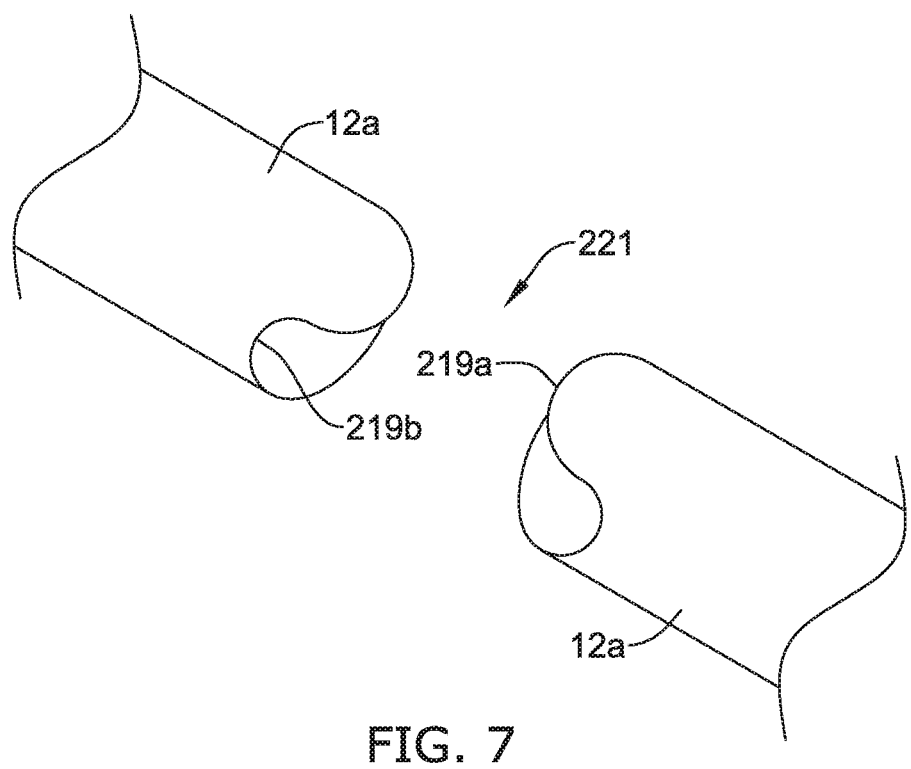
FIG. 7 illustrates the example stent shown in FIG. 6 in a fragmented state.

FIG. 7 illustrates the portions of first filament 12a (shown in FIG. 6) remaining after the first filament 12a in contact with the catalyst 222 has dissolved, thereby leaving a gap 221 between the non-dissolved portions of the first filament 12a. It can be appreciated that the general shape of the first filament 12a remaining after the biodegradation process may mirror the general shape of the activation material 220 disposed thereon (shown in FIG. 6). For example, FIG. 7 illustrates that the curved portions 219b shown in FIG. 7 may mirror the curved portions 219a described with respect to FIG. 6.

It can be appreciated that the activation material described above may be applied to the surface of the tubular scaffold 16 (described above) in a variety of configurations, shapes, arrangements, etc. such that the dissolution and/or fragmentation process of the tubular scaffold 16 may be customized and/or controlled. For example, the activation material 20 may be applied along the tubular scaffold 16 such that the scaffold 16 progressively dissolves into numerous small, uniform fragments. Alternatively, the activation material 20 may be applied along the tubular scaffold 16 such that the scaffold 16 dissolves into pieces of varying size.

In some instances, it may be beneficial to have the biodegradable tubular scaffold 16 (described above) dissolve in a specific sequence and/or progression. For example, in some instances it may be desirable to have the tubular scaffold 16 dissolve from its distal end to its proximal end. One method of controlling the sequence and/or progression of dissolution of the tubular scaffold 16 may be to dispose different activation materials having different types and/or concentrations of catalyst material along different portions of the tubular scaffold 16. It can be appreciated that the different concentrations of catalyst material will dissolve different portions of the tubular scaffold at different rates, thereby permitting a controlled the rate of dissolution of different portions of the tubular scaffold 16.

Figure 8:
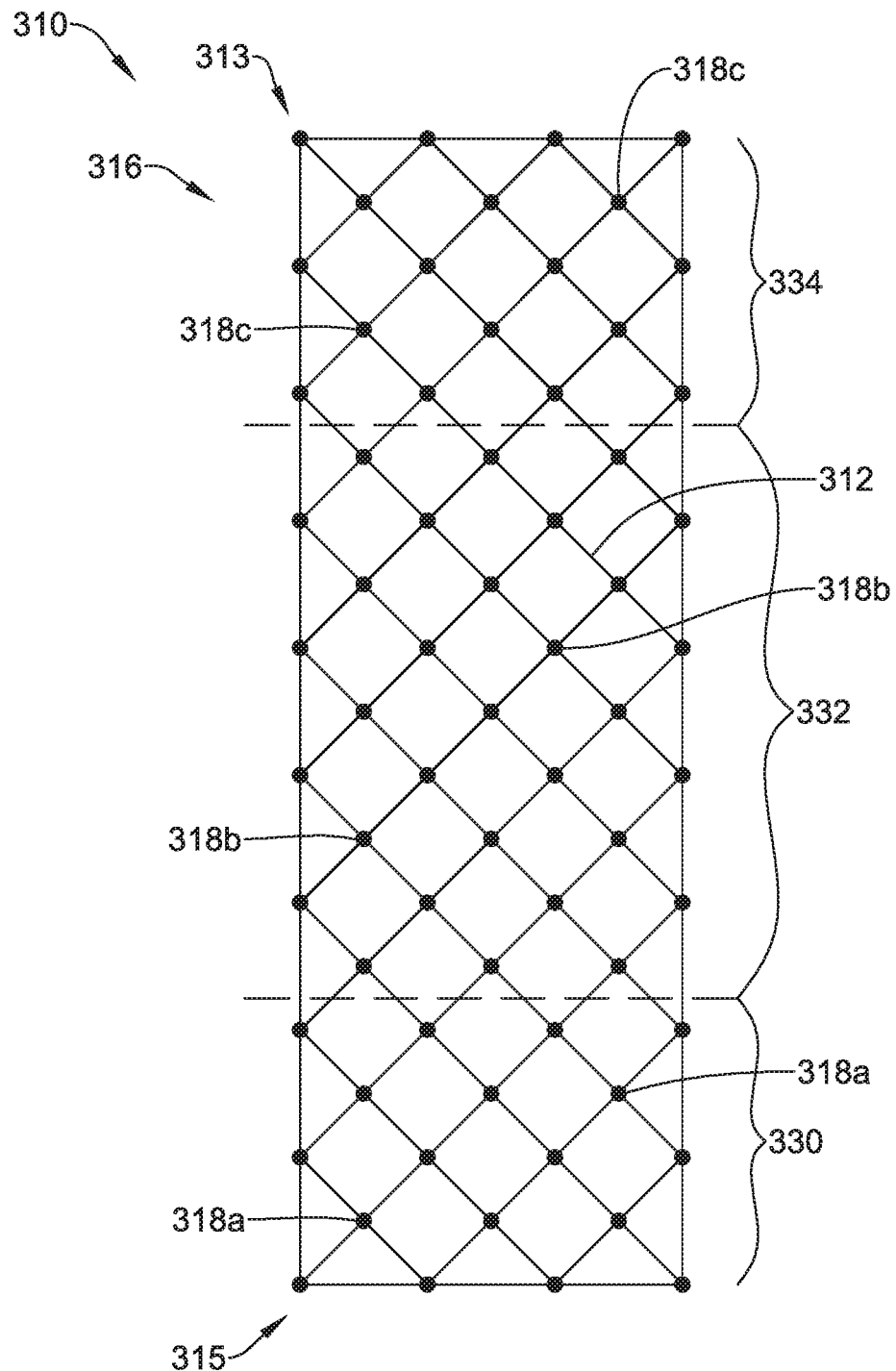
FIG. 8 illustrates another example stent.

For example, FIG. 8 illustrates an example stent 310 including an example tubular scaffold 316. The tubular scaffold 316 may be similar in form and function to other tubular scaffolds described herein. For example, the tubular scaffold 316 may include one or more filaments 312 extending from a distal end 315 to a proximal end 313. Additionally, FIG. 8 further illustrates that the example tubular scaffold may include three (or more) types of activation sites 318a, 318b and 318c. It can be appreciated that each of the activation sites 318a, 318b and 318c may include different catalysts, each of which may have a different type, quantity and/or concentration of catalyst designed to dissolve material at different rates. Further, FIG. 8 illustrates that each type of activation site 318a, 318b and 318c may be disposed in a particular region of the tubular scaffold 316. For example, the activation sites 318a may be disposed in a distal end region 330, the activation sites 318c may be disposed in a proximal end region 334 and the activation sites 318b may be disposed in a medial region 332 located between the distal end region 330 and the proximal end region 334.

As discussed above, it can be appreciated that if the activation sites 318a, 318b and 318c disposed within the regions 330, 332 and 334, respectively, include catalyst material designed to dissolve the filaments 312 of the tubular scaffold 316 at different rates (e.g., the catalyst in region 330 dissolves material faster than the catalyst in region 332, which, in turn, dissolves material faster than the catalyst in region 334), different regions of the tubular scaffold 316 may dissolve generally sequentially.

Figure 9:
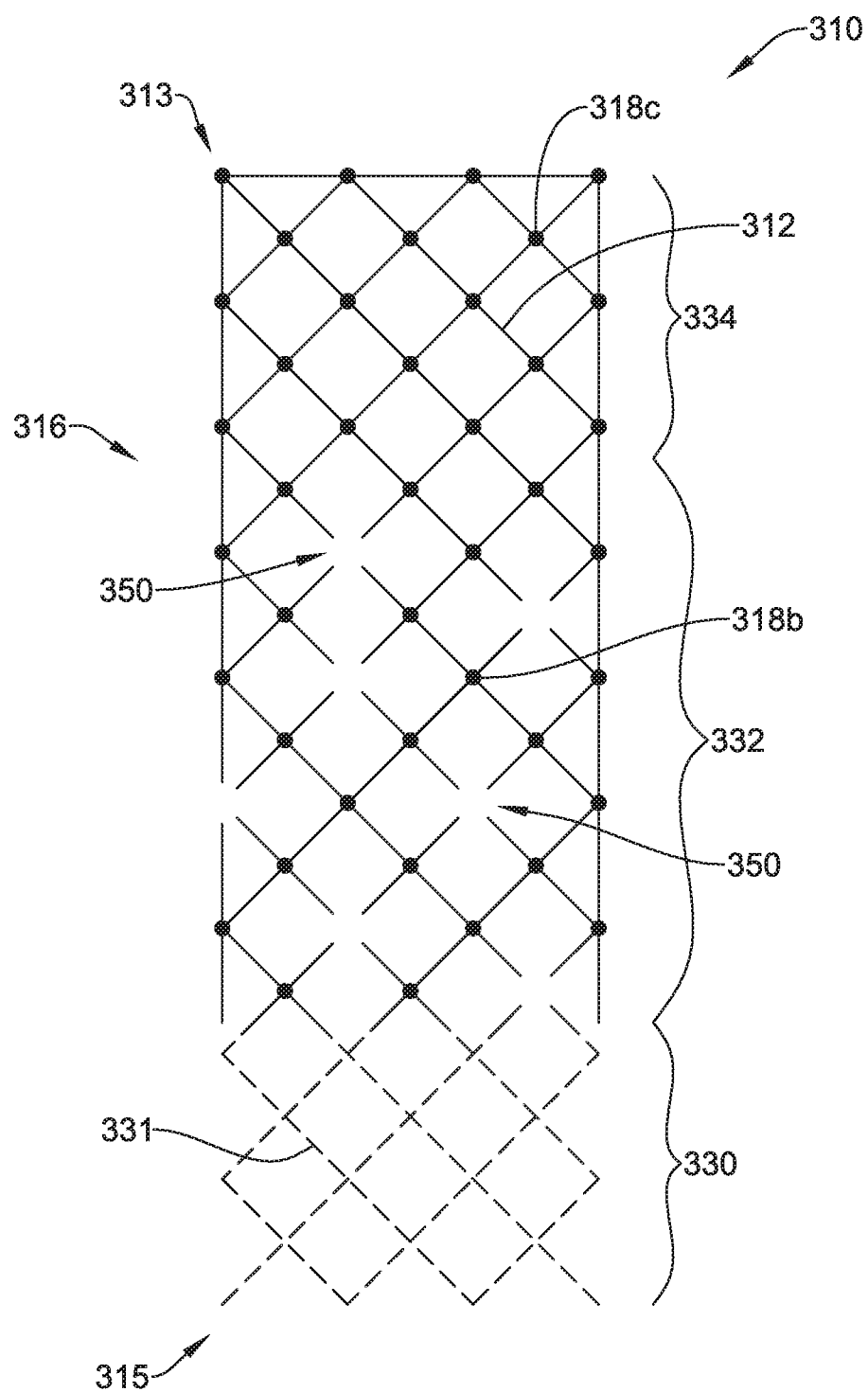
FIG. 9 illustrates the example stent shown in FIG. 8 undergoing a degradation process.

For example, FIG. 9 illustrates the tubular scaffold 316 (shown in FIG. 8) dissolving in a progressive manner from the distal end 315 to the proximal end 313. In particular, FIG. 9 illustrates the region 330 of the tubular scaffold 316 having the fastest dissolution rate (shown by the dashed lines 331), followed by the partial dissolution of the region 332 (FIG. 9 shows some activation sites 318b having been dissolved 350), followed by region 334 (whereby FIG. 9 shows that the filaments 312 nor the activation sites 318c have appreciably begun to dissolve as compared to the regions 330, 332). In other words, FIG. 9 generally illustrates the progressive dissolution of the tubular scaffold 316 from the distal end 315 of the tubular scaffold 316 to the proximal end 313 of the tubular scaffold 316.

Figure 10:
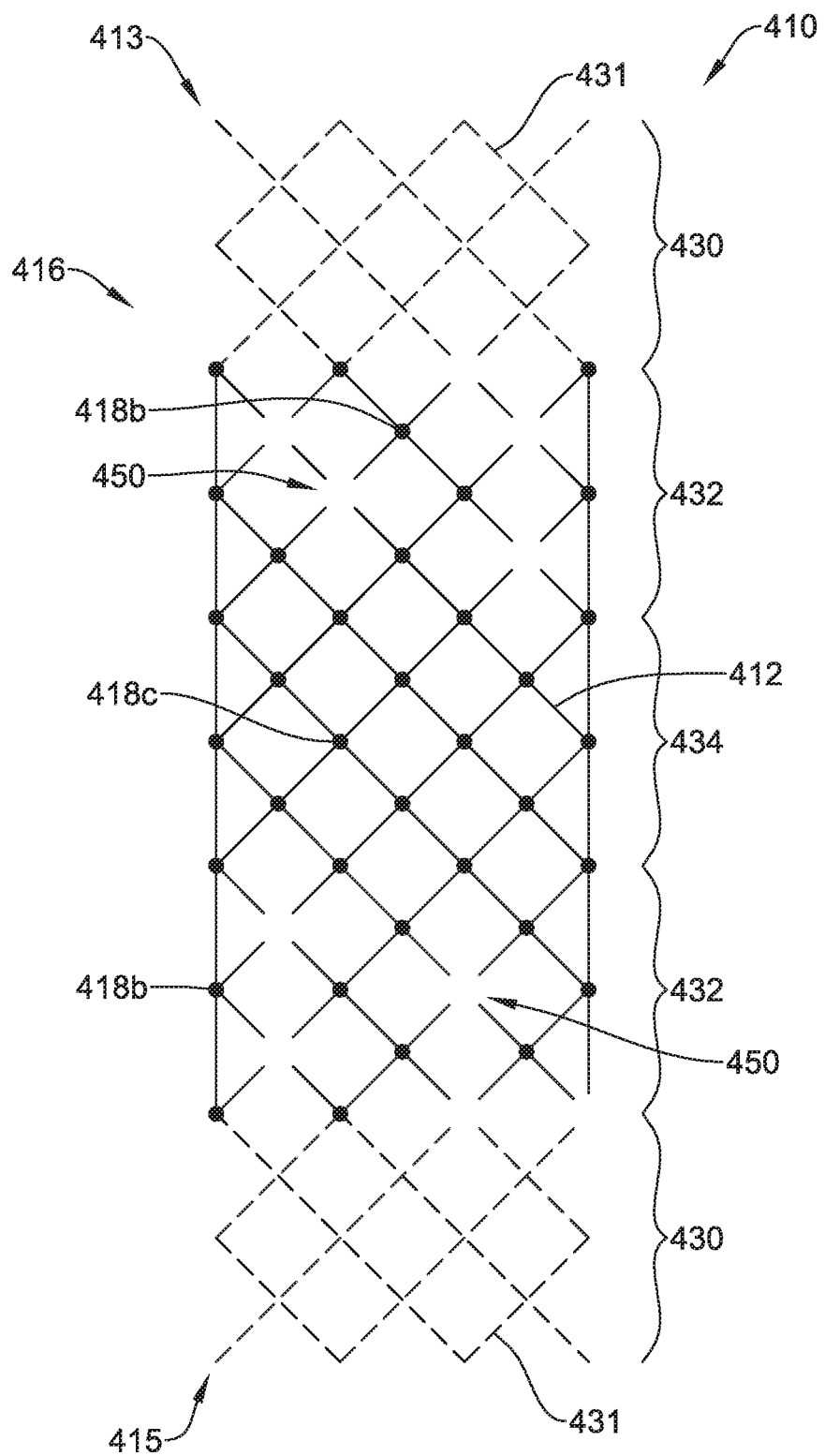
FIG. 10 illustrates another example stent undergoing a degradation process.

FIG. 10 illustrates another example stent 410 including an example stent 410 including an example tubular scaffold 416. The tubular scaffold 416 may be similar in form and function to other tubular scaffolds described herein. For example, the tubular scaffold 416 may include one or more filaments 412 extending from a proximal end 413 to a distal end 415. Additionally, similar to the example described with respect to FIG. 8 and FIG. 9, FIG. 10 illustrates that the example tubular scaffold 416 may include three regions 430, 432 and 434, each having activation sites of varying biodegradation rates. In other words, it can be appreciated that each of the three regions 430, 432 and 434 may include different catalyst material, each of which is designed to dissolve material at a different rate.

Further, FIG. 10 illustrates that the catalyst material present in the regions 430, 432 and 434 may be designed such the tubular scaffold 416 dissolves "inwardly" from each of the proximal end 413 and the distal end 415 toward the medial region 434. For example, FIG. 10 illustrates the regions 430 of the tubular scaffold 316 having the fastest dissolution rate (shown by the dashed lines 431), followed by the partial dissolution of the regions 332 (FIG. 10 shows some activation sites 418b having been dissolved 450), followed by regions 434 (whereby FIG. 10 shows that neither the filaments 412 nor the activation sites 418c have appreciably begun to dissolve as compared to the regions 330, 332).

Figure 11:
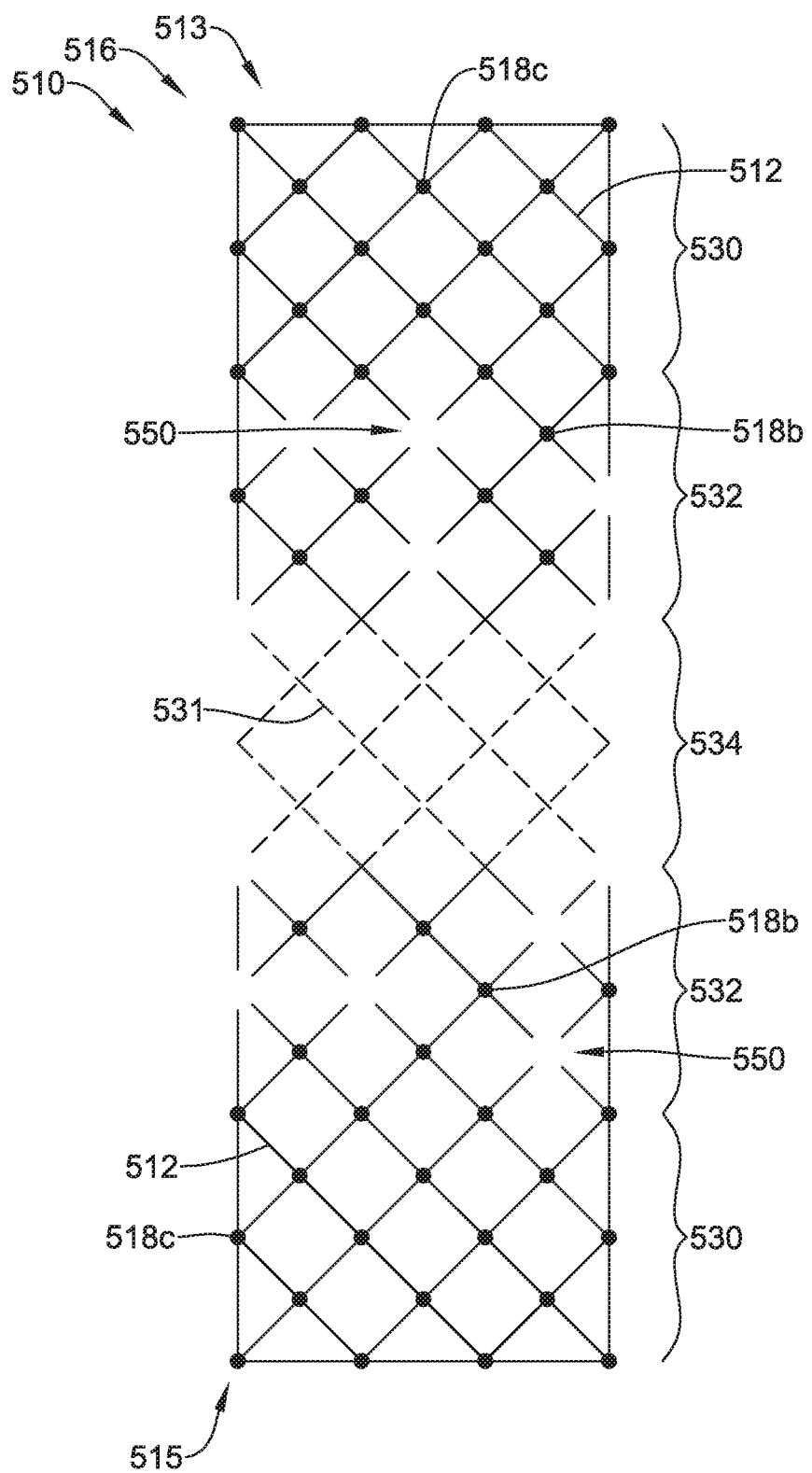
FIG. 11 illustrates another example stent undergoing a degradation process.

FIG. 11 illustrates another example stent 510 including an example tubular scaffold 516. The tubular scaffold 516 may be similar in form and function to other tubular scaffolds described herein. For example, the tubular scaffold 516 may include one or more filaments 512 extending from a proximal end 513 to a distal end 515. Additionally, similar to the example described with respect to FIGS. 8-10, FIG. 11 illustrates that the example tubular scaffold 516 may include three regions 530, 532 and 534, each having activation sites of varying biodegradation rates. In other words, it can be appreciated that each of the three regions 530, 532 and 534 may include different catalyst material, each of which is designed to dissolve material at a different rate.

Further, FIG. 11 illustrates that the catalyst material in the regions 530, 532 and 534 may be designed such the tubular scaffold 516 dissolves from the central region 534 of the tubular scaffold "outward" toward each of the proximal end 513 and the distal end 515. For example, FIG. 11 illustrates the region 534 of the tubular scaffold 516 having the fastest dissolution rate (shown by the dashed lines 531), followed by the partial dissolution of the regions 532 (FIG. 11 shows some activation sites 518b having been dissolved 550), followed by the regions 530 (whereby FIG. 11 shows that neither the filaments 512 nor the activation sites 518c have appreciably begun to dissolve as compared to the regions 532, 534).

It can be appreciated from the above discussion that the biodegradable stent designs disclosed herein are not limited to three different degradation regions and/or rates. For example, it is contemplated that one or more or the stent designs disclosed herein may further comprise two, three, four, five, six, or more biodegradable regions and/or materials, whereby each of the biodegradable regions and/or materials may have a different degradation rate. The example stents disclosed herein may be constructed of strategically placed portions of each different biodegradable region and/or material such that the stent degradation is progressive and staged in certain specific locations on the stent.

In some examples, it may be desirable to design the stent 10 (shown in FIG. 1) such that the degradation of the stent 10 can be precisely controlled. For example, in some instances, it may be desirable to minimize the size of the stent fragments as the stent 10 progressively dissolves. Further, it may be beneficial to design the stent 10 such that the stent 10 dissolves into fragments which are small enough as to not cause adverse medical complications at regions of the body near the stent implantation site.

Figure 12:
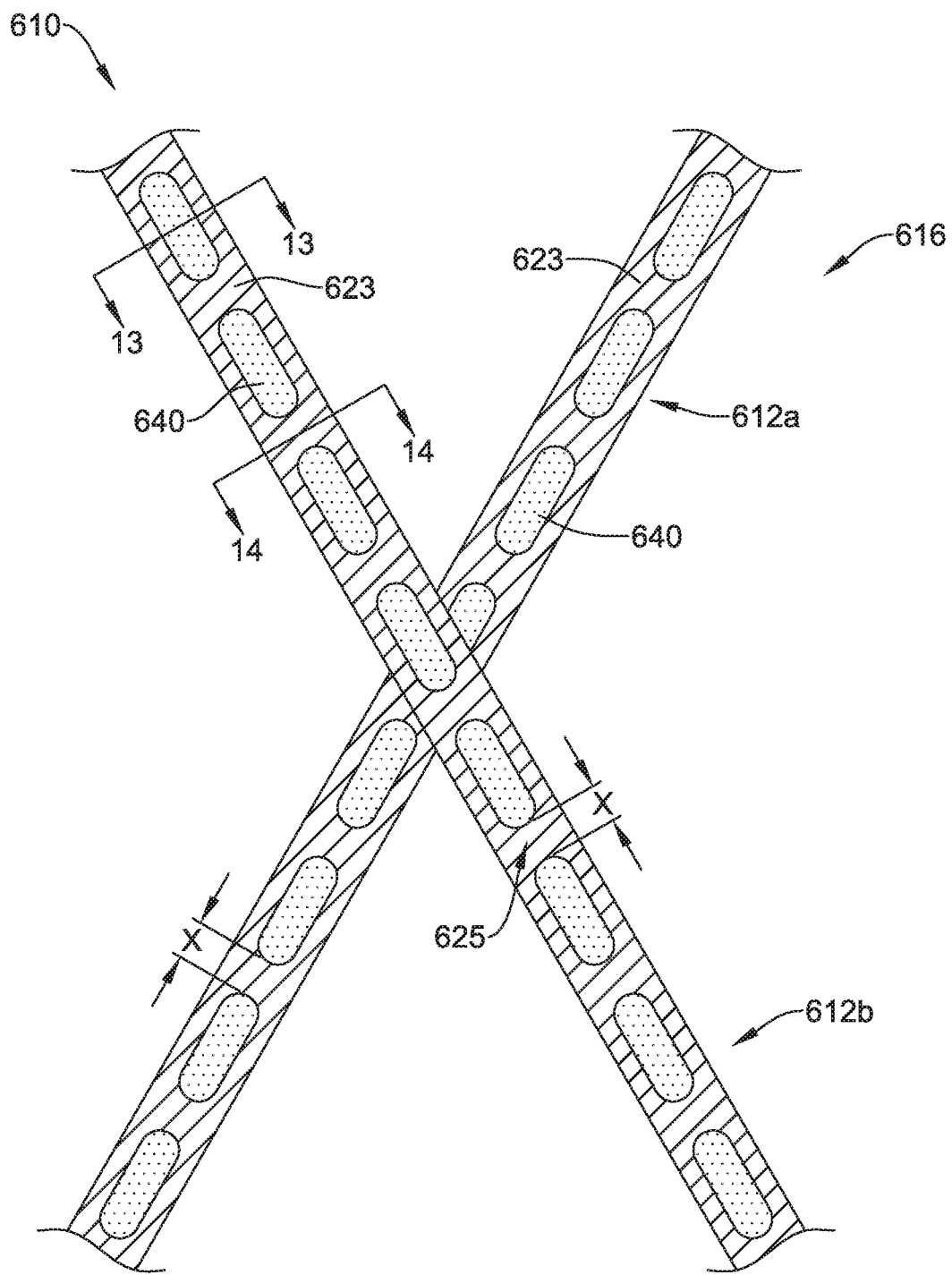
FIG. 12 illustrates another portion of an example stent.

FIG. 12 illustrates a portion of another example stent 610. The stent 610 may be similar in form and function to the stent 10 described above. For example, the stent 610 may include a tubular scaffold 616 which includes a first filament 612a and a second filament 612b. Each of the first filament 612a and the second filament 612b may be constructed from a first biodegradable material 623.

As illustrated in FIG. 12 (and will be further discussed with respect to FIG. 13), the stent 610 may also include a second biodegradable material 640 which may be encased within the cross-section of the first biodegradable material 623 of either the first filament 612a and/or the second filament 612b at discontinuous locations along the length of the first filament 612a and/or the second filament 612b. As shown in FIG. 12, the portion 625 of either the first filament 612a and/or the second filament 612b extending between two adjacent biodegradable regions 640 may include only the first biodegradable material 623. In other words, the first filament 612a and/or the second filament 612b may be constructed from the first biodegradable material 623 extending continuously along the length of the first filament 612a and/or the second filament 612b, whereby the second biodegradable material 640 may be encased and dispersed therein along discrete, spaced apart, and thus discontinuous locations along the length of the first filament 612a and/or the second filament 612b, leaving portions of the length of the first filament 612a and/or the second filament 612b devoid of the second biodegradable material 640.

FIG. 12 further illustrates that the biodegradable regions 640 may be separated from one another by a distance "X." However, while FIG. 12 illustrates that each of the biodegradable regions 640 may be spaced away from one another uniformly (e.g., each region 640 separated by a distance "X"), it is contemplated that in some examples, two or more of the biodegradable regions 640 may be separated from one another by variable distances.

Figure 13:
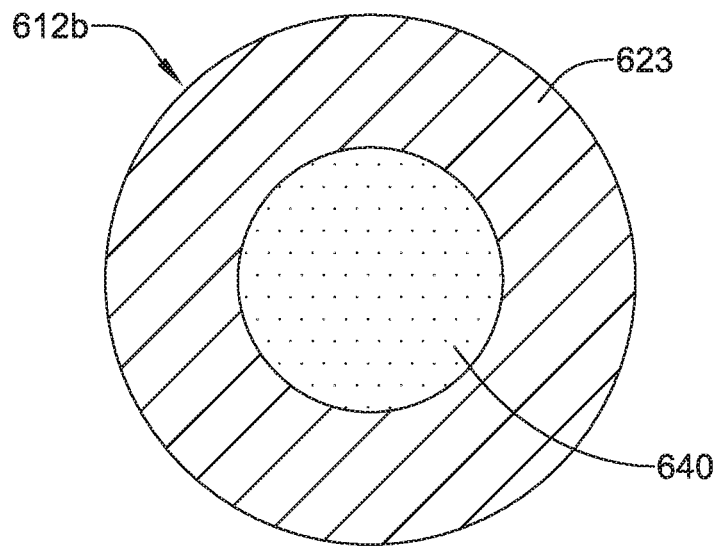
FIG. 13 illustrates a cross section along line 13-13 of the stent portion shown in FIG. 12.

FIG. 13 illustrates a cross-section of the second filament 612b taken along line 13-13 of FIG. 12. As described above, FIG. 13 illustrates the second biodegradable material 640 encased within the first biodegradable material 623. In other words, FIG. 13 illustrates that first biodegradable material 623 may surround the second biodegradable material 640 at discrete cross-sections of the second filament 612b. It is noted that the cross-section shown in FIG. 13 would be representative of cross-sections taken at discrete locations through the first filament 612a as well.

Figure 14:
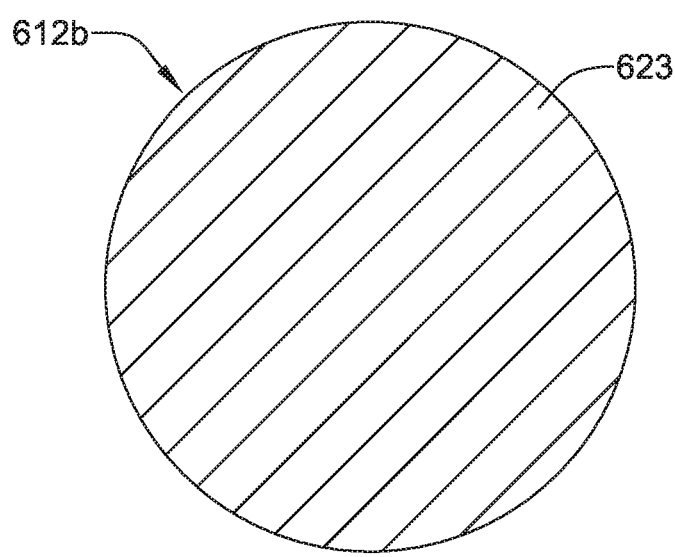
FIG. 14 illustrates a cross section along the line 14-14 of the stent portion shown in FIG. 12.

FIG. 14 illustrates a cross-section of the second filament 612b taken along line 14-14 of FIG. 12. As described above, FIG. 14 illustrates that the second filament 612b includes cross-sections that are devoid of the second biodegradable material 640 (described with respect to FIG. 13). In other words, FIG. 14 illustrates that the entire cross-section of the second filament 612b at other discrete cross-sections of the second filament 612b may include only the first biodegradable material 623. It is noted that the cross-section shown in FIG. 14 would be representative of cross-sections taken at discrete locations through the first filament 612a as well.

Regarding FIG. 13, in some examples, the first biodegradable material 623 and/or second biodegradable material 623 may include a biodegradable metal. In other examples, the first biodegradable material 623 and/or second biodegradable material 623 may include a biodegradable polymer. Further, in some examples, the first biodegradable material 623 may include a biodegradable polymer while the second biodegradable material 640 may include a biodegradable metal, or vice versa. Additionally, in some examples, the first biodegradable material 623, the second biodegradable material 640 or both the first biodegradable material 623 and the second biodegradable material 640 may include multiphasic materials having multiphasic properties.

Multiphasic materials disclosed herein may have heterogeneous structures within the material, typically on a microscopic scale (i.e. microstructure). Further, multiphasic materials may include beneficial characteristics such as variable degradation rates between the various heterogeneous phases. The multiphasic materials may have varying mechanical properties which may permit various medical devices to be specifically tailored to specific applications within the body. For example, stent scaffolds may be tailored for specific applications in the body. In addition, multiphasic materials may be beneficial for use in a dynamic environment, including repeated or cyclical loading, temperature variations and chemical environmental variability. Additionally, in some examples, multiphasic materials may be comprised of composites with different mixtures of a first biodegradable material and a second biodegradable material.

Additionally, in some instances, the stent 610 may be designed such that the first biodegradable material 623 may dissolve at a first biodegradable rate and the second biodegradable material 640 may dissolve at a second biodegradable rate, different from the first biodegradable rate. For instance, the rate of degradation of the second biodegradable material 640 may be slower than the rate of degradation of the first biodegradable material 623. It can be appreciated that by designing the second biodegradable material 640 to dissolve at a slower rate than the first biodegradable material 623, the size (e.g., length, width, etc.) of the second biodegradable material 640 may dictate the resulting particle size into which the tubular scaffold fragments.

Figure 15:
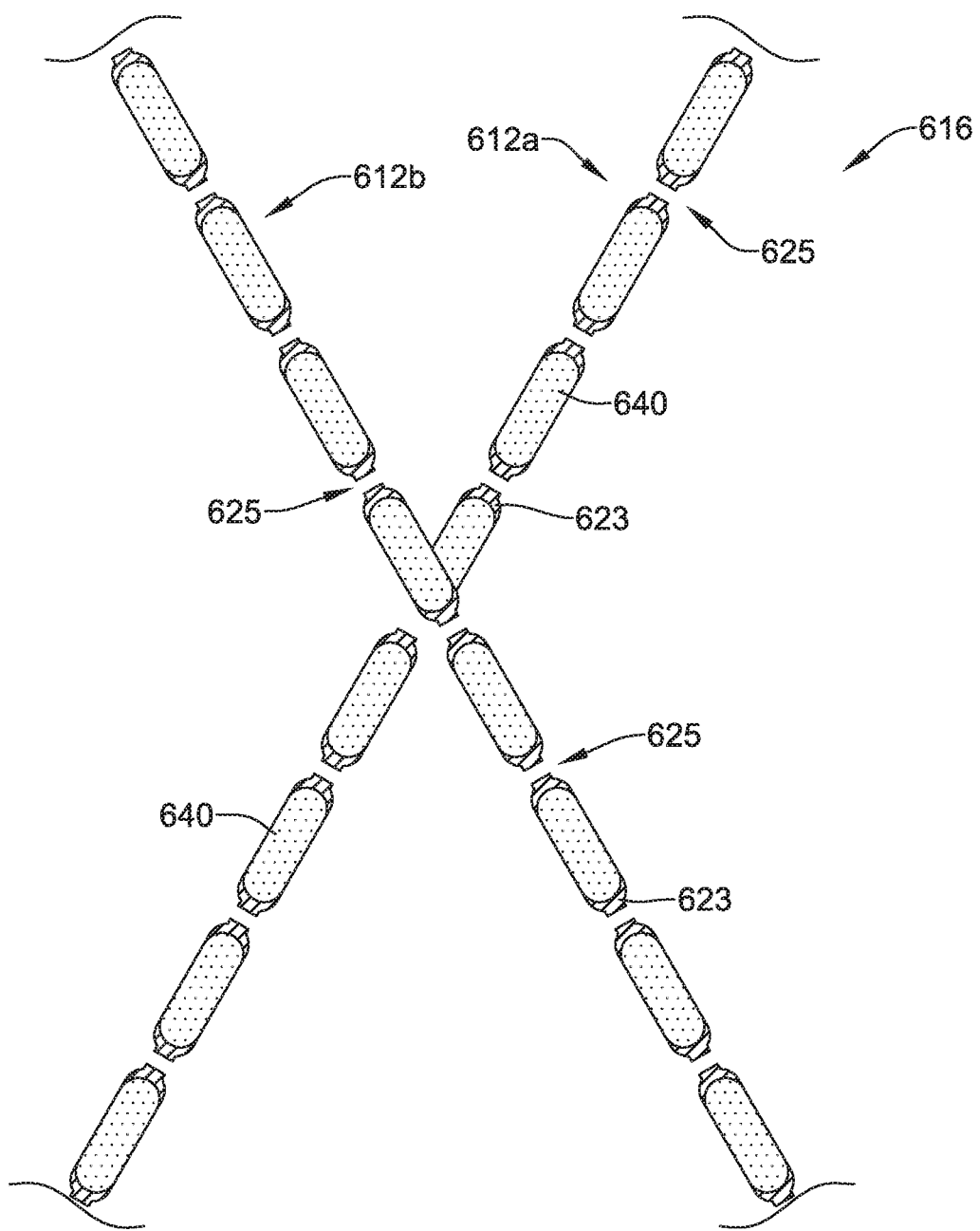
FIG. 15 illustrates the example stent portion shown in FIG. 12 undergoing a degradation process.

For example, FIG. 15 illustrates the partial degradation of the tubular scaffold 616 (including the partial degradation of the first filament 612a and the second filament 612b). As shown in FIG. 15, the first biodegradable material 623 has dissolved at a faster rate than the second biodegradable material 640. In other words, a greater percentage of the first biodegradable material 623 has dissolved relative to the second biodegradable material 640.

Additionally, FIG. 15 shows that portion 625 of each of the first filament 612a and the second filament 612b has dissolved such that the regions of first filament 612a and the second filament 612b including the second biodegradable material 640 separated from one another, and thus are no longer connected to one another. It can be appreciated that this mechanism of dissolution may result in the tubular scaffold progressively dissolving from the filaments 612a, 612b shown in FIG. 14 into pieces approximately the size of the second biodegradable material 640 shown in FIG. 15. It can further be appreciated that the second biodegradable material 640 may eventually dissolve until the tubular scaffold 616 is fully absorbed by the body.

Figure 16:
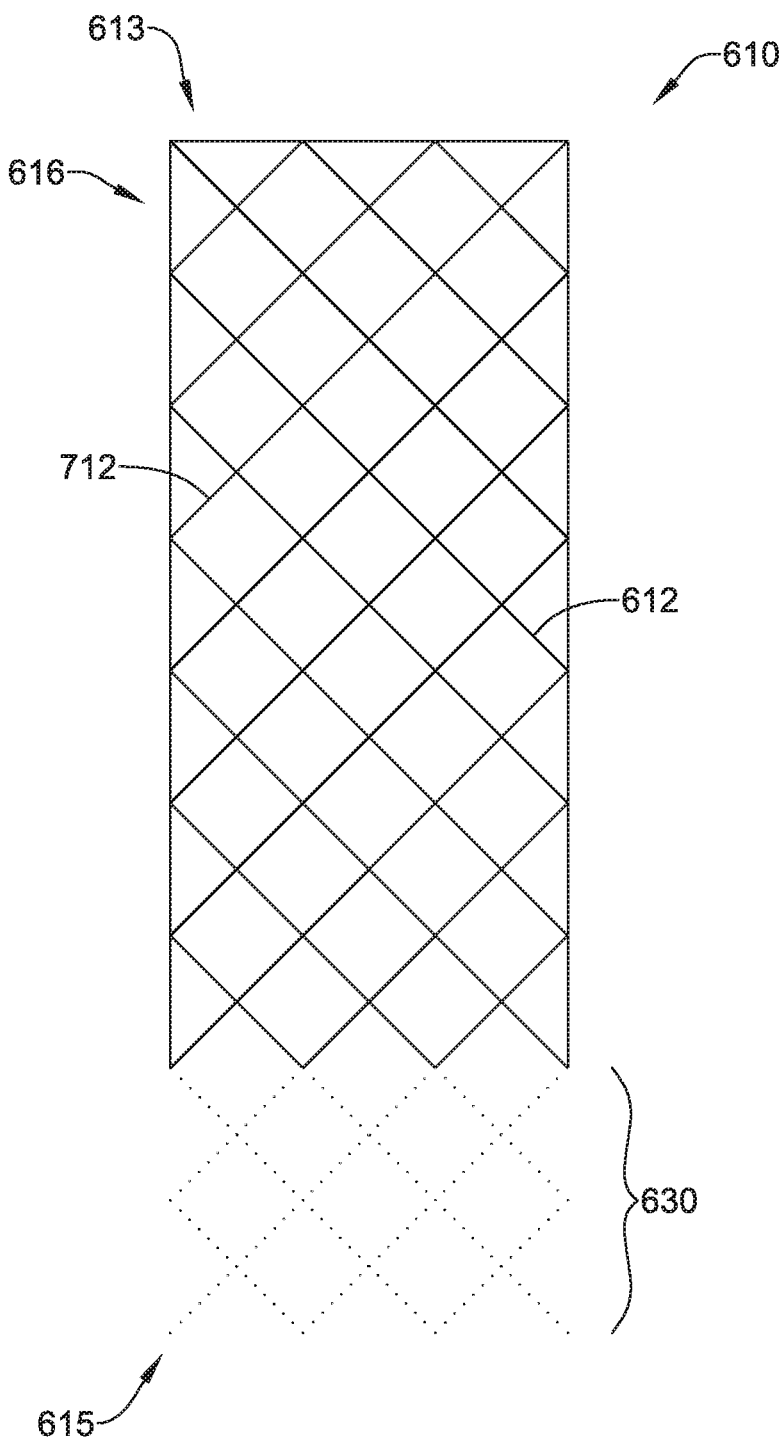
FIG. 16 illustrates another example stent undergoing a degradation process.

As discussed above, the size (e.g., length, width, etc.) of the second biodegradable material 640 may be tailored to customize the size of the particles desired during the dissolution of the tubular scaffold 616. For example, FIG. 16 illustrates the stent 610 (described above) including the tubular scaffold 616. The tubular scaffold 616 may include one or more filaments 612 (which may include the first filament 612a and/or the second filament 612b described above) extending from a proximal end 613 to a distal end 615. Further, FIG. 16 illustrates that the tubular scaffold 616 may include a distal end region 630 which has dissolved into very fine fragmented particles (shown by the dotted lines 631) via the dissolution process described above with respect to FIG. 14 and FIG. 15. In other words, the distal end region 630 shown in FIG. 16 may include the arrangement of the second biodegradable material 640 relative to the first biodegradable material 623 as described in FIG. 14 and FIG. 15. As described above, it can be appreciated that by altering the size, shape, placement, arrangement, etc. of the segments including the second biodegradable material 640 (as described above) relative to the segments including only the first biodegradable material 623 (as described above), the ultimate size and progression of biodegradation may be precisely controlled.

Similarly to that discussed above, in some examples a catalyst (not shown) may be designed to accelerate the biodegradation of the tubular scaffold 616 with which the catalyst may be in contact. The catalyst may be disposed along the outer surface of the first filament 612a and/or the second filament 612b. The catalyst may be designed to accelerate the biodegradation of the portions of the first filament 612a and/or the second filament 612b with which it contacts. Additionally, the catalyst may include an enzyme. For example, the catalyst may include (but is not limited to) proteases, esterases, glycosidases, manganese peroxidases, and/or similar materials. Further, it is contemplated that for examples in which the tubular scaffold 616 is constructed of a biodegradable polymer, the catalyst may be designed to include an enzyme which is designed to break down (e.g., biodegrade) the particular biodegradable polymer utilized to construct the tubular scaffold 616 (e.g., the material utilized to construct the first filament 612a and/or the second filament 612b). The enzymes contemplated herein may include, but are not limited to, plant enzymes, microbial enzymes, mammalian enzymes and/or human enzymes.

In yet other examples, a catalyst (not shown) designed to accelerate the biodegradation of the tubular scaffold 616 with which the catalyst may be in contact may include one or more ferric particles. In some examples, the ferric particle catalysts may be activated via inductive heating using an MRI. Additionally, it is contemplated that other heat sources may be utilized to activate the ferric particle catalyst. As discussed above, activation of the ferric catalyst may cause material in contact with the catalyst (e.g., material used to construct the tubular scaffold 616) to degrade at an accelerated rate relative to tubular scaffold material which is not in contact with the catalyst.

Figure 17:
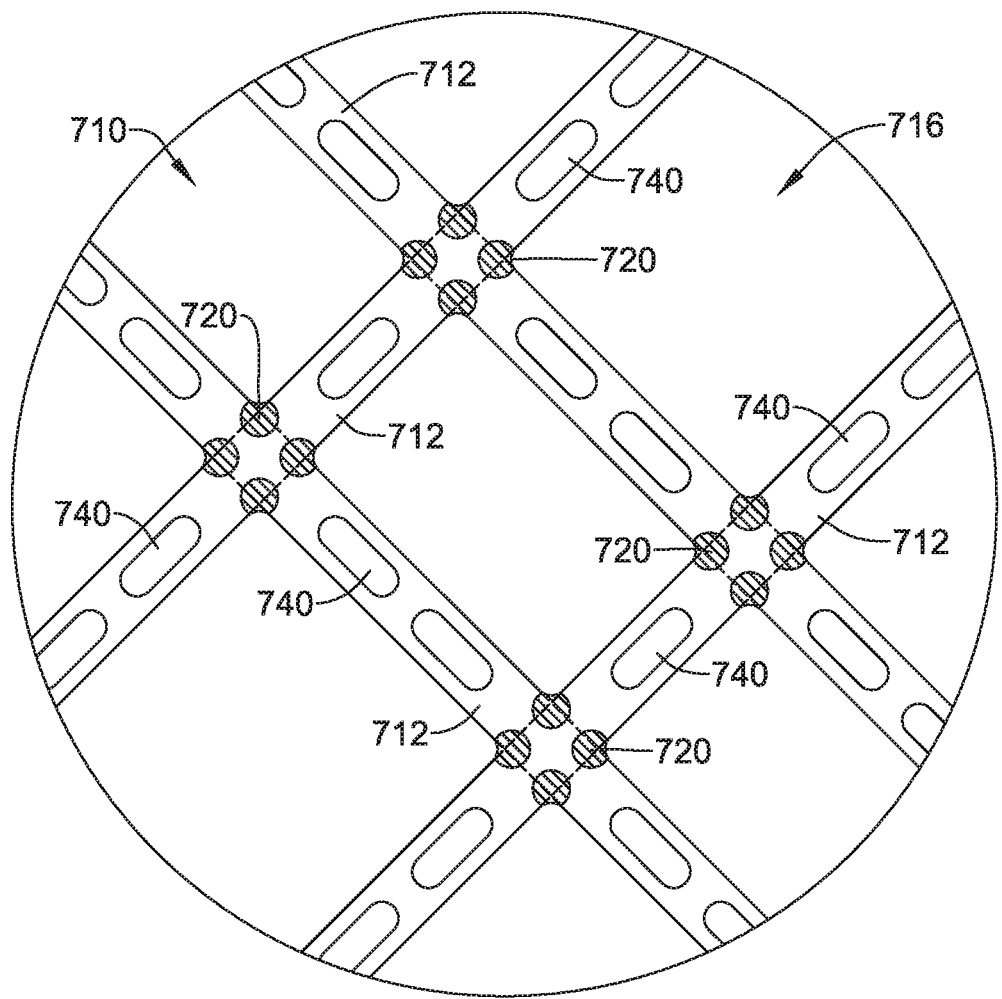
FIG. 17 illustrates another portion of an example stent.

FIG. 17 illustrates a portion of another example stent 710. The stent 710 may be similar in form and function to other stent examples described herein. For example, the stent 710 may include one or more filaments 712 arranged relative to one another to form a tubular scaffold 16. Additionally, FIG. 17 illustrates that the tubular scaffold 716 may include one or more activation sites 720 disposed thereon. The activation sites 720 may be similar in form and function to other activation sites described herein. For example, the activation sites 720 may include an activation material including a catalyst designed to accelerate the degradation of material with which the catalyst comes in contact. Further, FIG. 17 illustrates that the tubular scaffold 716 may include one or more biodegradable regions 740 which are designed to biodegrade as a rate slower than the material surrounding the biodegradable regions 740 (similar to the dissolution mechanism described above with respect to FIGS. 12-16).

It can be appreciated that the stent design illustrated in FIG. 17 may combine the beneficial characteristics of both the activation sites and the embedded biodegradable materials, as described above. For example, the stent 710 may progressively degrade in a desired sequence (e.g., as described above with respect to FIGS. 8-11) while also dissolving into very fine fragmenting particles via the dissolution process described above with respect to FIG. 14 and FIG. 15. It can be appreciated that the activation sites 720 and the biodegradable regions 740 may arranged with the tubular scaffold 716 in a variety of different configurations, depending on the desired dissolution properties for the stent 710.

The materials that can be used for the various components of stent 10 (and/or other stents disclosed herein) and the various tubular members disclosed herein may include those commonly associated with medical devices. For simplicity purposes, the following discussion makes reference to stent 10. However, this is not intended to limit the devices and methods described herein, as the discussion may be applied to other similar stent members and/or components of stent members or devices disclosed herein.

Stent 10 and/or other components of stent 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stent 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of stent 10 to achieve the same result.

In some embodiments, a degree of Magnetic Resonance Imaging (MRI) compatibility is imparted into stent 10. For example, stent 10, or portions thereof, may be made of a material that does not substantially distort the image and create substantial artifacts (e.g., gaps in the image). Certain ferromagnetic materials, for example, may not be suitable because they may create artifacts in an MRI image. Stent 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:
1. A stent, comprising:
  a tubular scaffold having a first end, a second end and a lumen extending therein, the tubular scaffold including:
    a first filament extending between the first end and the second end;

a first biodegradable region positioned at a discrete location longitudinally adjacent to a second biodegradable region such that the first biodegradable region is located closer to the first end than the second biodegradable region, wherein at least a portion of the first filament defines the first biodegradable region, wherein at least a portion of the first filament defines the second biodegradable region, and wherein each of the first biodegradable region and the second biodegradable region extends circumferentially around the lumen of the tubular scaffold;

wherein the first biodegradable region of the tubular scaffold is configured to degrade at a first rate of degradation;

wherein the second biodegradable region of the tubular scaffold is configured to degrade at a second rate of degradation;

wherein the first rate of degradation is faster than the second rate of degradation such that the first biodegradable region degrades at a faster rate than the second biodegradable region; and wherein the first biodegradable region includes a first catalyst disposed on the first filament, and wherein the second biodegradable region includes a second catalyst disposed on the first filament.

2. The stent of claim 1, wherein the first catalyst is configured to degrade the first biodegradable region at the first rate of degradation.

3. The stent of claim 2, wherein the first catalyst includes an enzyme.

4. The stent of claim 2, wherein the first catalyst includes a ferric particle.

5. The stent of claim 2, wherein the first catalyst is configured to be activated by an activation source, wherein the activation source triggers the first catalyst to accelerate the rate of degradation of the first biodegradable region.

6. The stent of claim 5, wherein the activation source includes an activation fluid.

7. The stent of claim 5, wherein the activation source includes inductive heating.

8. The stent of claim 2, wherein the tubular scaffold further comprises a second filament positioned adjacent to the first filament at a first activation site, and wherein the first catalyst extends between the first filament and the second filament.

9. The stent of claim 2, wherein the second catalyst is configured to degrade the second biodegradable region at the second rate of degradation.

10. The stent of claim 1, wherein the first biodegradable region includes a first biodegradable material and a second biodegradable material, and wherein the second biodegradable material is encased in the first biodegradable material.

11. The stent of claim 10, wherein the rate of degradation of the second biodegradable material is slower than the rate of degradation of the first biodegradable material.

12. The stent of claim 10, wherein the first biodegradable region, the second biodegradable region, or both the first and the second biodegradable regions include a multiphasic material.

13. The stent of claim 10, wherein the second biodegradable region is devoid of the second biodegradable material.

14. The stent of claim 13, wherein the second biodegradable region includes a catalyst disposed on the first filament.

15. A stent, comprising:
a tubular scaffold having a first end and a second end, the tubular scaffold including:
a plurality of filaments extending between the first end and the second end, the plurality of filaments including a first filament and a second filament,
wherein the first filament crosses the second filament at a first activation site, and wherein the first filament crosses the second filament at a second activation site such that the first activation site is closer to the first end than the second activation site; and
a first activation material including a first catalyst disposed along the first activation site, a second activation material including a second catalyst disposed along the second activation site, wherein the first catalyst is configured to dissolve portions of the first and second filaments in contact with the first catalyst at a faster rate than portions of the first and second filaments which are in contact with the second catalyst.

16. The stent of claim 15, wherein the first catalyst includes an enzyme.

17. The stent of claim 15, further comprising a third activation site located along the first filament, and wherein a third catalyst is disposed along the third activation site, and wherein the degradation rate of the third catalyst is different from the degradation rate of the first catalyst and the second catalyst.

18. A stent, comprising;
a tubular scaffold having a first end and a second end, the tubular scaffold including:
a plurality of filaments extending between the first end and the second end;
a first tubular biodegradable region positioned at a discrete location longitudinally adjacent to a second tubular biodegradable region such that the first tubular biodegradable region is located closer to the first end than the second tubular biodegradable region, wherein each of the first tubular biodegradable region and the second tubular biodegradable region defines a tubular region extending circumferentially entirely around a lumen of the tubular scaffold;
wherein the plurality of filaments defining the first tubular biodegradable region includes a plurality of first biodegradable portions arranged around the tubular region of the first tubular biodegradable region, and wherein the plurality of filaments defining the second tubular biodegradable region includes a plurality of second biodegradable portions arranged around the tubular region of the second tubular biodegradable region;
wherein the first biodegradable portions located within the first tubular biodegradable region are configured to degrade at a first rate of degradation;
wherein the second biodegradable portions located within the second tubular biodegradable region are configured to degrade at a second rate of degradation; and
wherein the first rate of degradation is faster than the second rate of degradation such that the first tubular biodegradable region having the first biodegradable portions fully degrades faster than the second tubular biodegradable region having the second biodegradable portions;

further comprising a first catalyst disposed along discrete portions of each of the plurality of filaments in the first tubular biodegradable region, wherein the first catalyst includes an enzyme;
wherein the plurality of filaments in the second tubular biodegradable region are devoid of the first catalyst;
wherein the plurality of filaments in the second tubular biodegradable region include a second catalyst different from the first catalyst.

\* \* \* \* \*